United States Patent
Grundler et al.

(10) Patent No.: US 7,425,587 B2
(45) Date of Patent: Sep. 16, 2008

(54) FLOWABLE UNDERFILLING MATERIAL

(75) Inventors: Andreas Grundler, Wuppertal (DE);
Albert Erdrich, Bad Nauheim (DE);
Michael Greczmiel, Frankfurt (DE);
Claus-Peter Ernst, Mainz (DE)

(73) Assignee: Heraecus Kulzer GmbH, Hanau (DE)

( * ) Notice: Subject to any disclaimer, the term of this patent is extended or adjusted under 35 U.S.C. 154(b) by 158 days.

(21) Appl. No.: 11/050,591

(22) Filed: Feb. 3, 2005

(65) Prior Publication Data

US 2005/0192375 A1    Sep. 1, 2005

(30) Foreign Application Priority Data

Feb. 10, 2004    (DE) ............... 10 2004 006 643

(51) Int. Cl.
*C08F 2/46* (2006.01)
*C08J 3/28* (2006.01)
*C08J 3/20* (2006.01)
*A61K 6/083* (2006.01)
*A61K 6/087* (2006.01)

(52) U.S. Cl. .................. 522/81; 522/74; 522/83; 522/44; 522/100; 522/170; 522/90; 522/181; 522/182; 522/113; 522/120; 522/121; 522/122; 522/174; 522/175; 523/109; 523/113; 523/115; 523/116; 523/117; 523/118; 523/120

(58) Field of Classification Search .......... 522/71, 522/44, 81, 83, 100, 170, 181, 182, 113, 522/120, 121, 122, 133, 90; 523/109, 111, 523/113, 116, 115, 117, 118, 120
See application file for complete search history.

(56) References Cited

U.S. PATENT DOCUMENTS

| | | | |
|---|---|---|---|
| 4,134,935 A | 1/1979 | Quiring et al. ........ 260/859 R |
| 4,372,836 A | 2/1983 | Schmitt et al. ........ 204/159.23 |
| 4,588,763 A | 5/1986 | Brannstrom et al. ........ 524/77 |
| 4,746,686 A | 5/1988 | Waller ........ 522/14 |
| 4,871,786 A | 10/1989 | Aasen et al. ........ 523/113 |
| 5,698,020 A | 12/1997 | Salz et al. ........ 106/35 |
| 6,309,221 B1 | 10/2001 | Jensen |
| 6,528,555 B1 | 3/2003 | Nikutowski et al. ........ 523/116 |
| 6,670,436 B2 | 12/2003 | Burgath et al. ........ 526/213 |
| 2002/0193463 A1 | 12/2002 | Jones et al. ........ 523/115 |

FOREIGN PATENT DOCUMENTS

| | | |
|---|---|---|
| DE | 20 57 978 | 5/1972 |
| DE | 21 40 404 | 2/1973 |
| DE | 19520016 C2 | 11/1996 |
| EP | 0287213 | 10/1988 |
| EP | 0 363 095 | 4/1990 |
| GB | 2257433 | 1/1993 |
| WO | WO 83/02557 | 8/1983 |
| WO | WO 0025729 | 5/2000 |

OTHER PUBLICATIONS

Krejci et al.; Time requirement to remove totally bonded tooth-colored posterior restorations and related tooth substance loss; Dent Matter 11; 34-40 (January 1995).

Szep S et al.; Revision of Composite Resin Restorations: Influence on Cavity Dimensions and Time as a Function of the applied Materials; Deutsche Zahnarztliche Zeitschrift 57; 219-226 (2002).

*Primary Examiner*—Sanza L McClendon
(74) *Attorney, Agent, or Firm*—Norris, McLaughlin & Marcus PA

(57) ABSTRACT

A flowable, light-curing underfilling material that is easily visible and distinguishable from the tooth substance. The underfilling material contains
at least one polymerizable monomer,
at least one polymerization initiator and also
0.3-10% white pigment.

9 Claims, No Drawings

FLOWABLE UNDERFILLING MATERIAL

The invention concerns a flowable underfilling material (liner) that is inserted in the prepared tooth cavity before applying the composite fillings.

BACKGROUND OF THE INVENTION

For a long time, adhesive restorations of the lateral tooth in the form of an amalgam[1] have played an important role in the field of restorative therapy and are usually used these days without any additional underfilling. Only in the case of indirect restoration such as ceramic inlays and ceramic crowns, a reconstructive underfilling is still considered to be a meaningful process. However, this reconstructive underfilling can also consist of an adhesively attached stump construction composite.

The function of the underfilling—protecting the tooth from chemical, thermal and mechanical noxa—is taken over by dentin adhesion; provided that it is used correctly, because only then can it avoid a post-operative disorder on the one hand and can provide a bacteria-proof sealing to the dentin: The bacterial penetration alongside open dentin tubules is one of the main reasons for applying a filling. In the most disadvantageous case, bacteria or toxins can penetrate into the pulp via the dentin tubules and cause a case of pulpitis or an infected necrosis. However this can be avoided by sealing the surface sufficiently with a dentin adhesive as effectively as by using an underfilling. Then the metal-free reconstruction made of composite or ceramics also takes care of the thermal and mechanical protection of the dentin wound.

The following is an argument that is difficult to invalidate for the use of separate underfillings: If a composite filling would have to be removed again, it is a laborious procedure for the therapist to remove tooth-colored composite from deep areas near the pulp or at the cervical cavity border completely [2][2]. Often more tooth substance is removed than necessary [3, 4, 5][3][4][5], and often this results in an iatrogenic exposure of the pulp. In addition, Krejci specifies the increased time factor in the composite revision with an average revision time of 24 minutes compared to, for example, 11 minutes with glass isonomer cement and 15 minutes with amalgam fillings [2]. Other authors state shorter revision times in composite restorations [6][6], but also describe a relatively longer treatment time as regards other materials that are not tooth-colored.

In general and according to manufacturer's instructions, a composite filling should not have to be removed again at all since it promises lifelong durability. However the clinical reality shows a different picture: here, a composite restoration has to be removed every now and then even though composite materials can be repaired by all means. As to the possibility of repairs, adhesive composite restorations are clearly superior to other restoration materials. However, there are individual indications that call for a complete removal of the entire composite material from the cavity. It is not possible for the therapist to simply move into the cavity along its brown edge. Besides, there is always the risk of causing injury to the pulp in deep areas near the pulp. Often, for reasons of "safety" more tooth substance is removed than is actually necessary: Millar et al. describe that in the revision of composite fillings, the cavities iatrogenically increase up to 37% [6].

There have been experiments already to cope with this problem by marking the dental materials with a photochromic dye (DE19520016C2). The photochromic dye contained in the dental materials changes color for a short period of time to olive-brown when exposed to a polymerization lamp, and the therapist can then discern whether he is still working in the area of the filling. The development led to the product "Tetric® Flow Chroma" of the company Vivadent, Liechtenstein. Szep et al. [5] examined the application of Tetric Flow Chroma in an in vitro-study. Surprisingly they found a significant reduction of the loss of tooth substance during the revision of the fillings only when Tetric Flow Chroma was applied also on the cavity walls and not exclusively on the cavity floor. Also no significant reduction of the revision time could be determined during the use of Tetric Flow Chroma exclusively on the cavity floor, or even during the use of the material on all cavity borders. This may be partly due to the necessary additional light activation of the photochromic substances with the polymerization lamp. The light exposure had to take place several times, the color change did not remain for an excessively long period of time and could additionally be activated by a thinner filling during the normal routine checkup of restorations. This, in turn, gave the therapist an "unpleasant feeling," if a brown shimmer were noticeable below the restorations. Since of course the therapist always has to remove restorations of another person, but never his own, the question that remains unanswered here is whether this brown shimmer is a caries existing below the filling or whether it is the application of Tetric Flow Chroma. There is also the requirement for suitable underfilling materials that do not cause any baseless suspicion of caries.

In addition, adhesives with properties of color change under the effect of light are suggested (U.S. Pat. No. 6,528,555 B1), wherein the color change is permanent. Dental materials with reversible color change have also been described in U.S. Pat. No. 6,670,436 B2.

The task underlying the invention is to make available a flowable, light-curing underfilling material for composite fillings that is clearly visible after curing during or following the removal of a composite filling lying on it. This underfilling is distinguishable from the tooth substance without further measures such as additional lighting.

It is necessary to find a compromise between the goals of achieving full opacity, white color and complete curing of more than 1 mm (determined as per ISO-norm 4049) in light polymerization. This 1 mm originates from the specification of ISO norm 4049 for opaque filling materials.

It is important to implement a high opacity of the bright white colored flow composite, since such a material is used only in a thin layer. If a demarcation material of this type had the same opacity as a conventional flow composite, it would not be discernable on the tooth substance despite its white color. The setting of an appropriate high opacity is technically no problem, as opposed to the subsequent light-curing of the material. The more opaque a light-curing material is, the fewer layer thicknesses can be polymerized in a polymerization cycle.

SUMMARY OF THE INVENTION

Surprisingly it is possible to solve the problem described above by the measured use of a bright white contrast coloration in a flowable underfilling composite for marking the transition to the natural tooth substance with a high color contrast.

Thus a flowable, light-curing underfilling material results, that is easily visible and is distinguishable from the tooth substance. This underfilling material contains A) at least one polymerizable monomer B) at least one polymerization initiator C) 0.3-10% white pigment.

DETAILED DESCRIPTION

The advantage in using bright white pigments is the permanent coloration that requires no separate light activation or the like. The differentiation in terms of color of natural tooth substance is a method that is already being used successfully for quite some time. The contrast colors blue, gray or even snow-white enable the quick identification of the remaining materials in the preparation border. A blue contrast color of this type is contained in the light-curing stump construction composite Rebilda LC (VOCO, Cuxhaven). With that one could achieve significantly reduced revision times as compared with all other comparison groups (Tetric Ceram with Tetric Flow, Tetric Flow Chroma on the cavity floor and with Tetric Flow Chroma on all cavity surfaces). One also partly achieved reduced substance loss (exception: no significant difference to the group in which Tetric Flow Chroma was also applied on the cavity walls) [5].

The use of white as a contrast color has the following advantages for the filling therapy: It does not simulate any deep caries below the restorations and it least disturbs the total aesthetic appearance when a white-colored material is applied on the cavity walls, e.g. also on the cervical shoulder of the approximal box.

The apprehension that a bright white underfilling material could cause unaesthetic white stripes or bands on the cavity edge has not been confirmed in practice. On the contrary, the high degree of whiteness of the underfilling can be an advantage if some tooth substance that is discolored by amalgam residue receives an optical lucency.

Known oxides with high refraction index are considered for usage as white pigments, such as for example $Al_2O_3$, $ZrO_2$, $ZnO$ or $TiO_2$. Of these, $TiO_2$ is preferred. The white pigments can be present in the mixture advantageously in an amount of 0.3-10%.

The monomers considered for use are those that are conventionally used in the dental field. Of these, the preferred monomers include methacrylates or acrylates. Examples are monofunctional monomers that are capable of radical polymerization such as mono(meth)acrylamide and mono(meth)acrylates, acrylamide, methacrylamide, N-ethylacrylamide, methyl-, ethyl-, butyl-, benzyl-, furfuryl- or phenyl(meth)acrylate.

Polyfunctional monomers are the known polyfunctional acrylates and/or methacrylates such as for example bisphenol-A-di(meth)acrylate, Bis-GMA (an addition product made of methacryl acid and bisphenol-A-diglycidylether), UDMA (an addition product made of 2-hydroxyethylmethacrylate and 2,2,4-hexamethylene diisocyanate), di-, tri- or tetraethylene glycol di(meth)acrylate, decandioldi(meth)acrylate, trimethylolpropanetri(meth)acrylate, pentaerythrittetra(meth)acrylate and butanedioldi(meth)acrylate, 1,10-decanedioldi(meth)acrylate or 1,12-dodecanediol di(meth)acrylate.

Examples of fillers considered for usage besides the white pigments mentioned above are metal oxides such as alumina, zirconia, tin oxide, titania, metal sulfates, dental glasses, pyrogene or precipitated silicic acids, aluminosilicate glasses, fluoroaluminosilicate glasses, quartz, strontium silicate, strontium borosilicate, lithium silicate, lithium aluminium silicate, amorphous silicic acids, phyllosilicates, zeolites or combinations thereof.

Preferred photoinitiators are benzophenone, benzoin and their derivatives or alpha-diketones or their derivatives such as 9,10-phenanthrene quinone, diacetyl or 4,4-diclorobenzyl. Camphorquinone and 2,2-dimethoxy-2-phenylacetophenone are used with particular preference as also alpha-diketones in combination with amines as reduction agents such as for example 4-(N,N-dimethylamino)-benzoic acid ester, N,N-dimethylaminoethylmethacrylate, N,N-dimethyl-sym.-xylidine or triethanolamine. In addition, even acylphosphines such as for example 2,4,6-trimethylbenzoyldiphenyl- or bis(2,6-dichlorobenzyl)-4-N-propylphenyl phosphine oxide are particularly suitable.

The flowable underfilling material in accordance with the invention has in its structural composition/structural composition test by means of rotation viscometry (Paar Physica rheometer UDS 200, method cone/plate, measuring cone MK 20 (25 mm, 1°) smooth; measuring plate 180° smooth, temperature 23+/−0.1° C.) a shear viscosity of 6.0 to 100 Pa·s (medium measured at 100/sec shear rate, measurement after 30 sec. shearing) and 125 to 400 Pa·s (medium measured at 0.05/sec shear rate, measured 10 sec after drop in the shear rate from 100/sec to 0.05/sec). In the cone/plate measurement the specimen is located in a shearing gap between a very flat cone and a coaxial plate. An even shear rate distribution is generated in the measuring gap by the selection of the cone angle.

The implementation of the invention is elaborated more in detail on the basis of the following examples. The percentages mentioned in the remaining description refer to the weight:

EXAMPLE 1

A composition for an underfilling material in accordance with the invention has the following components:

| | |
|---|---|
| Bisphenol-A-propyloxy-dimethacrylate | 25.5% |
| TEDMA | 11.5% |
| Initiator complex | 1% |
| Ba—Al-silicate glass ($d_{50}$ = 0.985μ) | 60.5% |
| Silanized titanium dioxide | 0.5% |

The components were added together and processed under light shield in a mixer until homogenous.

EXAMPLE 2

The comparison of specimens with different degrees of whiteness shows its effect on the curing depth:

| | Sample | | | | | | |
|---|---|---|---|---|---|---|---|
| | 1 | 2 | 3 | 4 | 5 | 6 | ISO 4049 |
| Titanium white ($TiO_2$)% | 0.05 | 0.06 | 0.11 | 0.25 | 0.33 | 0.50 | No specifications |
| Curing depth with a 40 sec. light exposure using Translux CL determined as per ISO 4049 | >3 mm | >3 mm | >3 mm | 2.6 mm | 2.2 mm | 2 mm | 1.0 mm for opaque filling materials. |
| Transparency [%] | 42.9 | 43.1 | 35 | 23.9 | 18 | 11.2 | No specifications. |

Pastes with varying strengths of pigmentation were examined in accordance with the afore-mentioned table.

The transparency/translucence measurements were determined using a Datacolor chromatometer SF 600, specimen thickness 1.0 mm, diameter 20 mm, screen 18 mm, transparency measurement by measuring over black and white background (reference tile). The curing depth was determined in accordance with ISO 4049 and the illumination was provided using a Translux Energy lamp.

With a curing depth of 2 mm, specimen 6 proves to be an ideal compromise between sufficient covering power (opacity)—in order to be clearly visible during excavation and in order to cover sclerotized dentin—and a curing depth that is clearly greater than the ISO 4049 specification for filling materials. Since particularly in the case of deep cavities in the patient's mouth, the illumination device cannot be placed directly on the surface of the material to be polymerized, this higher curing depth at 2 mm is meaningful in practice.

Specimens with a clearly higher content of titanium dioxide also show a good covering power, but the curing depth drops further. A higher initiator concentration could partially compensate for this decline in the curing depth, but the pastes would then have a higher light-sensitivity and would be discolored to a potentially stronger yellowish color.

We claim:

1. Flowable and light-curing underfilling material that is visible and distinguishable from a tooth substance, comprising
   A) at least one polymerizable monomer
   B) at least one photo initiator
   C) titanium dioxide in an amount of from 0.3 wt. % to less than 0.74 wt. % at which a complete curing depth of more than 1 mm (determined as per ISO 4049) during 40 sec. light polymerization using a standard polymerization lamp for dental purposes will still result.

2. Underfilling material in accordance with claim 1, wherein component A is a (meth)-acrylate or acrylate monomer.

3. Underfilling material in accordance with claim 1, wherein component C is titanium dioxide.

4. Underfilling material in accordance with any one of claims 1, 2 or 3, further comprising
   D) further fillers selected from the group consisting of Dental glasses, metal oxides, metal sulfates, metal silicates and silicic acids.

5. Underfilling material in accordance with any one of claims 1, 2 or 3 further comprising
   E) a barium silicate glass.

6. Underfilling material in accordance with any one of claims 1, 2 or 3 having a shear viscosity of 6.0 to 100 Pa·s (medium measured at a shear rate of 100/sec., measurement after 30 sec. shearing) and 125 to 400 Pa·s (medium measured at a shearing rate of 0.05/sec., measured 10 sec. after the reduction of the shear rate from 100/sec. to 0.05/sec), determined in its structural composition/structural composition test by means of rotation viscometry (cone/plate, measuring cone 25 mm, 1°, smooth; measuring plate 180°, smooth, temperature 23+/−0.1° C.).

7. Process for the production of a flowable, light-curing underfilling material that is easily visible and distinguishable from the tooth substance, having a complete curing depth of more than 1 mm (determined as per ISO 4049) during 40 sec. light polymerization using a standard polymerization lamp for dental purposes, which comprises coloring said underfilling material to a bright white by adding titanium oxide thereto in an amount of from 0.3% wt. % to less than 0.74 wt. % at which a complete curing depth of more than 1 mm (determined as per ISO 4049) during 40 sec. light polymerization using a standard polymerization lamp for dental purposes will still result.

8. Method for coloring a flowable, light-curing underfilling material that is easily visible and distinguishable from the tooth substance, having a complete curing depth of more than 1 mm (determined as per ISO 4049) during 40 sec. light polymerization using a standard polymerization lamp, which comprises adding a titanium dioxide to said underfilling material in an amount of from 0.3% wt. % to less than 0.74 wt. % at which a complete curing depth of more than 1 mm (determined as per ISO 4049) during 40 sec. light polymerization using a standard polymerization lamp for dental purposes will still result.

9. Underfilling material in accordance with claim 1, wherein the amount of titanium dioxide is from 0.3 wt.% to 0.5 wt. %.

* * * * *